US012624395B2

(12) United States Patent　　　　(10) Patent No.:　US 12,624,395 B2
Lescure et al.　　　　　　　　　　　(45) Date of Patent:　　May 12, 2026

(54) PROCESS FOR IDENTIFYING A STRESS STATE AND/OR FOR ASSESSING THE STRESS RESPONSE LEVEL IN A SUBJECT

(71) Applicants: ADISSEO FRANCE S.A.S., Antony (FR); CENTRE NATIONAL DE LA RECHERCHE SCIENTIFIQUE, Paris (FR)

(72) Inventors: Alain Lescure, Strasbourg (FR); Luc Thomes, Yutz (FR); Yves Mercier, Montmarault (FR); Mickaël Briens, Montluçon (FR)

(73) Assignees: ADISSEO FRANCE S.A.S., Antony (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 1270 days.

(21) Appl. No.: 17/439,724

(22) PCT Filed: Mar. 13, 2020

(86) PCT No.: PCT/EP2020/056869
§ 371 (c)(1),
(2) Date: Sep. 15, 2021

(87) PCT Pub. No.: WO2020/187748
PCT Pub. Date: Sep. 24, 2020

(65) Prior Publication Data
US 2022/0154276 A1　　May 19, 2022

(30) Foreign Application Priority Data
Mar. 15, 2019　(EP) ..................................... 19163238

(51) Int. Cl.
*C12Q 1/68*　　　(2018.01)
*C12Q 1/6876*　　(2018.01)
*G01N 33/50*　　(2006.01)

(52) U.S. Cl.
CPC ....... *C12Q 1/6876* (2013.01); *G01N 33/5023* (2013.01); *C12Q 2600/158* (2013.01)

(58) Field of Classification Search
CPC ............ C12Q 1/6876; C12Q 2600/158; C12Q 1/6883; C12Q 2600/106
See application file for complete search history.

(56) References Cited

U.S. PATENT DOCUMENTS

2012/0142550 A1　6/2012　Zehnder et al.
2018/0237859 A1　8/2018　Redei et al.

FOREIGN PATENT DOCUMENTS

EP　　　2017623 A1　1/2009
WO　2009/052567 A1　4/2009

OTHER PUBLICATIONS

Probeset listing for Human Genome U133 Plus 2.0 Array from Affymetrix. Accessed Jul. 1, 2015. (Year: 2015).*
Yen et al. Cell Transplantation 2011; 20: 1529-1545 (Year: 2011).*
Neubauer et al. Journal of Applied Physiology 2014; 116: 274-287 (Year: 2014).*
Torun et al. Nigerian Journal of Clinical Practice 2017; 20: 1368-1403 (Year: 2017).*
Dunford et al. Maternal protein-energy malnutrition during early pregnancy in sheep impacts the fetal ornithine cycle to reduce fetal kidney microvascular development. The FASEB Journal 2014; 28: 4880-4892 (Year: 2014).*
Bouchama et al. A Model of Exposure to Extreme Environmental Heat Uncovers the Human Transcriptome to Heat Stress. Scientific Reports 2017; 7: 9429 (Year: 2017).*
May 12, 2020 International Search Report issued in International Patent Application No. PCT/EP2020/056869.
Sep. 16, 2021 International Preliminary Report on Patentability issued in International Patent Application No. PCT/EP2020/056869.
KRICKA; "Nucleic Acid Detection Technologies—Labels, Strategies, and Formats"; Clinical Chemistry; 1999; vol. 45; No. 4; pp. 453-458.
Loyau et al.; "Thermal manipulation of the chicken embryo triggers differential gene expression in response to a later heat challenge"; BMC Genomics; 2016; vol. 17; No. 329; pp. 1-15.
Campos et al.; "High ambient temperature alleviates the inflammatory response and growth depression in pigs challenged with *Escherichia coli* lipopolysaccharide"; The Veterinary Journal; 2014; vol. 200; pp. 404-409.
Rederstorff et al.; "Increased Muscle Stress-Sensitvity Induced by Selenoprotein N Inactivation in Mouse: A Mammalian Model for SEPN1-Related Myopathy"; PLOS ONE; 2011; vol. 6; No. 8; pp. 1-13.
"Affymetrix GeneChip Human genome U133 Array Set HG-U133A", NCBI, Gene Expression Omnibus, Accession Display+, https://www.ncbi.nlm.nih.gov/geo/query/acc.cgi?acc=GPL96 (2002), pp. 1-4.

* cited by examiner

*Primary Examiner* — Gary Benzion
*Assistant Examiner* — Olayinka A Oyeyemi
(74) *Attorney, Agent, or Firm* — Oliff PLC

(57) ABSTRACT

A process for identifying a stress state in a subject, for assessing the stress response level in a subject, for predicting the efficacy of an intervention solution in a subject, for monitoring the efficacy of an intervention solution in a subject and/or for identifying an intervention solution for a subject, having a step of detecting the expression and/or quantifying the expression level, in a sample of the subject, of at least four genes selected from a group made of twenty-six genes, as well as a kit having a way for amplifying and/or detecting the expression of the genes, and uses thereof.

6 Claims, 8 Drawing Sheets

PROCESS FOR IDENTIFYING A STRESS STATE AND/OR FOR ASSESSING THE STRESS RESPONSE LEVEL IN A SUBJECT

FIELD OF THE INVENTION

The present invention relates to a process for identifying a stress state in a subject, for assessing the stress response level in a subject, for predicting the efficacy of an intervention solution in a subject, for monitoring the efficacy of an intervention solution in a subject and/or for identifying an intervention solution for a subject, comprising a step of detecting the expression and/or quantifying the expression level, in a sample of said subject, of at least four genes selected from a group consisting of twenty-six genes, as well as a kit comprising means for amplifying and/or detecting the expression of said genes, and uses thereof.

BACKGROUND OF THE INVENTION

Stress is commonly defined, as proposed by Hans Selye in its 1956' seminal book "The stress of life" (Edition: McGraw-Hill Book Company), as "a state manifested by a specific syndrome, which consists of all non-specifically induced changes within a biological system". In particular, stress is a physiological state, wherein individuals exposed to modifications of biotic or abiotic factors, called stressors or challenges, in the environment initiate a response to maintain homeostasis. This stress response will first induce behavioral, biological and physical changes in these individuals, that can ultimately result in tolerance and adaptation. In case adaptation is not completed or fails, the tolerance threshold may be exceeded, resulting in altered biological functions. The inability of an individual to withstand stress or to cope with environmental challenges may lead to many unfavorable consequences, ranging from discomfort to death.

In particular, in animal production, a wide range of abiotic stressors has been identified, such as social interactions or rough handling, common farm practices (e.g. castration, dehorning, teeth clipping, shoeing, weaning crowding), improper feeding, exposure to adverse climatic conditions, exercise, work and transport. Stressor exposure occurring during the rearing period is likely to influence the preservation of animal well-being, productivity and performance. Animal growth parameters (such as weight gain, feed intake, Feed Conversion Ratio, mortality and morbidity) are traditionally used to characterize animal performance, but they do not specifically reflect animal stress state. It is therefore essential to be able to identify stress state in a subject (human or animal), through the use of sensitive and robust diagnostic tools.

Some stress biomarkers have previously been proposed among circulating hormones (e.g. cortisol, ACTH, adrenalin, ocytocine, vasopressin), catabolism products, such as accumulation of oxidated lipids (e.g. malondialdehyde, isoprostanes, hydroperoxides, oxydated LDL, hexanoyl-lysine) or accumulation of oxidated proteins (e.g. nitrotyrosine, carbonylated proteins), inflammation biomarkers (e.g. hydrogen peroxide, myeloperoxidase), biomarkers of oxidated DNA (e.g. 8-hydroxy-2'-deoxyguanosine), or the measure of the activity of intracellular antioxidant systems (e.g. superoxide dismutase, peroxiredoxines, thioredoxines, glutaredoxines, glutathion peroxidases, glutathion). On this basis, kits have also been developed, such as the Oxyscale diagnostic kit (as described in the patent EP2017623) or the QIAGEN Oxidative stress $RT^2$ profiler PCR arrays, which rely on the measure of the expression of a large number of genes.

Various genes have also been described as being involved in particular cellular models of stress, but it is well-known to the person skilled in the art that results obtained in vitro are rarely translatable in vivo, and it cannot be deduced from these studies which of these genes, if any, could be useful for identifying a stress state in a subject (human or animal).

Overall, all these biomarkers show several limitations, in particular because they are often transient, and specific of the type of stressor and/or the species considered.

Indeed, these biomarkers are not easily transferrable between species and/or stress conditions, and no satisfactory universal biomarker has been identified yet.

In this context, it was discovered by the inventors, completely unexpectedly, that the detection and/or quantification of the expression of at least four genes selected in a list of twenty-six genes is useful to circumvent these problems. These genes represent biomarkers which are independent of the type of stressors and the species considered.

DESCRIPTION OF THE INVENTION

Therefore, the present invention relates to an in vitro process for identifying the presence or absence of a stress state in a subject, and/or for assessing (and/or for quantifying) the stress response level in a subject, comprising a step of detecting the expression and/or quantifying the expression level, in a sample of said subject, of at least four genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc.

In the context of the present invention:

The term "stress" or "stress state", in relation with a subject, is to be understood as meaning a physiological state, wherein individuals exposed to modifications of biotic or abiotic factors, called "stressors" (or "stress factors" or "challenges"), in the environment initiate a response to maintain homeostasis. This "stress response" will first induce behavioral, biological and physical changes in these individuals, that can ultimately result in tolerance and adaptation. In case adaptation is not completed or fails, the tolerance threshold may be exceeded, resulting in altered biological functions. The inability of an individual to withstand stress or to cope with environmental challenges may lead to many unfavorable consequences, ranging from discomfort to death.

"Assessing the stress response level" in a subject goes beyond the mere identification of the presence or absence of a stress state in a subject; it may allow to categorize subjects according to their stress response level, and more particularly between the adapted and non-adapted subgroups. "Assessing the stress response level" encompasses the possibility of "quantifying the stress response level" in a subject;

An "adapted" subject is defined as a subject able to set an adequate response to stress as a consequence of stressor exposure; a "non-adapted" subject is defined as a subject not able to set an adequate response to stress as a consequence of stressor exposure;

The term "subject" or "individual" refers to a human or an animal;

The term "livestock animals" refers to domesticated animals raised in an agricultural setting to produce labor and various commodities;

"Pets" or "leisure animals" refer to animals, which are kept at home as companions (e.g. mammals, such as dogs and cats, as well as aquarium fish, aviary or caged birds);

An "intervention solution" corresponds to any type of intervention (e.g. a diet, a nutritional supplement, a pharmacological treatment, a rearing practice or a modification in the environment) on an individual, which is useful for limiting the impact of stress and/or reducing stress response level and/or increasing stress tolerance and/or stimulating adaptation of the individual. A "candidate intervention solution" corresponds to an intervention, which is to be tested to identify whether it is a relevant intervention solution, or not;

A gene is a sequence of DNA, which encodes a protein molecule. DNA is first converted into RNA (mRNA) by transcription, and said RNA is then converted into the protein molecule by translation. The detection and/or quantification of gene expression can therefore be carried out at the mRNA or at the protein level. In the present invention, genes are referred to by their names in humans (*Homo sapiens*), for convenience, but it is to be understood that, unless stated otherwise, this encompasses all the homologs of these genes in other species, and includes all possible inter-individual polymorphisms;

The expression of genes can be merely detected (presence/absence of the corresponding mRNA or protein), without necessarily any quantitative measurements, or it can also be quantified (i.e. gene expression at the mRNA or protein level is determined in a quantitative manner). Quantification of gene expression level may allow to identify the presence or absence of a stress state in a subject and/or to assess the stress response level (and possibly, to quantify the stress response level) in a subject.

Preferably, the present invention relates to an in vitro process for identifying the presence or absence of a stress state in a subject, and/or for assessing (and/or for quantifying) the stress response level in a subject, comprising a step of detecting the expression and/or quantifying the expression level, in a sample of said subject, of at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc.

Preferably, said at least four genes (or at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, or at least twenty-six genes) are different genes, which are respectively selected in each of the Lists 1 to 4 below:

List 1: Anxa1, Anxa2, Chac1, Postn, Col12a1, Gfpt2, Mgp, Thbs1, Tnc, Col1a1

List 2: Anxa1, Anxa2, Chac1, Postn, Mrc1, Serpinh1

List 3: Anxa1, Anxa2, Chac1, Postn, Lgals1, Cidea, Hmox1, Kctd12, Sh2b2, Slit3

List 4: Anxa1, Anxa2, Chac1, Postn, Col14a1, Efemp1, G0s2, Kera, Nes, Panx1, Runx1, Ankrd33b.

List 1 consists of the four genes conserved between the four models PN, CT, SN and PT (i.e. Anxa1, Anxa2, Chac1, Postn, "four most conserved genes"), and the genes which are conserved between the three models PT, PN and CT (Col12a1, Gfpt2, Mgp, Thbs1, Tnc, Col1a1 or "List 1A"). List 2 consists of the four most conserved genes, and the genes which are conserved between the three models PT, SN and CT (Mrc1, Serpinh1, or "List 2A"). List 3 consists of the four most conserved genes, and the genes which are conserved between the three models PT, PN and SN (Lgals1, Cidea, Hmox1, Kctd12, Sh2b2, Slit3, or "List 3A"). List 4 consists of the four most conserved genes, and the genes which are conserved between the three models CT, PN and SN (Col14a1, Efemp1, G0s2, Kera, Nes, Panx1, Runx1, Ankrd33b, or "List 4A"). When the at least four genes are respectively selected in each of the Lists 1 to 4 above, said at least four genes comprise at least three genes which have been identified in each of the PN, CT, SN and PT models, respectively.

More preferably, the present invention relates to an in vitro process for identifying the presence or absence of a stress state in a subject, and/or for assessing (and/or for quantifying) the stress response level in a subject, comprising a step of detecting the expression and/or quantifying the expression level, in a sample of said subject, of at least the four most conserved genes Anxa1, Anxa2, Chac1 and Postn. Even more preferably, the present invention relates to an in vitro process for identifying the presence or absence of a stress state in a subject, and/or for assessing (and/or for quantifying) the stress response level in a subject, comprising a step of detecting the expression and/or quantifying the expression level, in a sample of said subject, of at least the four most conserved genes Anxa1, Anxa2, Chac1 and Postn, and:

at least one, at least two, at least three, at least four, at least five, at least six of the genes of List 1A (Col12a1, Gfpt2, Mgp, Thbs1, Tnc, Col1a1);

at least one, at least two of the genes of List 2A (Mrc1, Serpinh1);

at least one, at least two, at least three, at least four, at least five, at least six of the genes of List 3A (Lgals1, Cidea, Hmox1, Kctd12, Sh2b2, Slit3); or at least one, at least two, at least three, at least four, at least five, at least six, at least seven, at least eight of the genes of List 4A (Col14a1, Efemp1, G0s2, Kera, Nes, Panx1, Runx1, Ankrd33b).

In a preferred embodiment, the present invention relates to an in vitro process for identifying the presence or absence of a stress state in a subject, and/or for assessing (and/or for quantifying) the stress response level in a subject, comprising a step of detecting the expression and/or quantifying the expression level, in a sample of said subject, of at least all the genes of List 1, at least all the genes of List 2, at least all the genes of List 3, or at least all the genes of List 4. In another preferred embodiment, the present invention relates to an in vitro process for identifying the presence or absence of a stress state in a subject, and/or for assessing (and/or for quantifying) the stress response level in a subject, comprising a step of detecting the expression and/or quantifying the expression level, in a sample of said subject, of at least the 26 genes Ankrd33b, Anxa1, Anxa2, Chac1, Cidea, Col1a1, Col12a1, Col14a1, Efemp1, G0s2, Gfpt2, Hmox1, Kctd12,

5

6

Kera, Lgals1, Mgp, Mrc1, Nes, Panx1, Postn, Runx1, Serpinh1, Sh2b2, Slit3, Thbs1 and Tnc.

Preferably also, the at least four, at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six genes in the in vitro process described above, comprise at least one, at least two, at least three, at least four, at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two genes selected from the group consisting of Anxa1, Anxa2, Chac1, Col1a1, Col12a1, Col14a1, Efemp1, Gfpt2, Hmox1, Kctd12, Kera, Lgals1, Mgp, Mrc1, Nes, Panx1, Postn, Runx1, Serpinh1, Slit3, Thbs1 and Tnc. More preferably, they comprise at least one, at least two, at least three, at least four, at least five, at least six, at least seven, at least eight, at least nine, at least ten, at least eleven, et least twelve, at least thirteen, at least fourteen, at least fifteen, at least sixteen, at least seventeen, at least eighteen genes selected from the group consisting of Anxa1, Anxa2, Col1a1, Col12a1, Col14a1, Efemp1, Hmox1, Lgals1, Mgp, Mrc1, Nes, Panx1, Postn, Runx1, Serpinh1, Slit3, Thbs1 and Tnc. Even more preferably, they comprise at least one, at least two, at least three, at least four, at least five, at least six, at least seven, at least eight, at least nine, at least ten, at least eleven, et least twelve, at least thirteen, at least fourteen genes selected from the group consisting of Anxa1, Anxa2, Col1a1, Col14a1, Efemp1, Lgals1, Mgp, Mrc1, Postn, Runx1, Serpinh1, Slit3, Thbs1 and Tnc. Even more preferably, they comprise at least one, at least two, at least three, at least four, at least five, at least six, at least seven, at least eight, at least nine, at least ten genes selected from the group consisting of Anxa1, Anxa2, Col1a1, Col14a1, Efemp1, Lgals1, Mgp, Postn, Slit3 and Thbs1. Even more preferably, they comprise at least one, at least two, at least three, at least four genes selected from the group consisting of Anxa2, Efemp1, Lgals1 and Postn.

The process as described above is useful for identifying the presence or absence of a stress state and/or for assessing (and/or for quantifying) the stress response level, in any type of subject (human or animal). Preferably, said subject is an animal, and particularly a livestock animal or a leisure animal. More preferably, said subject is an animal selected from the group consisting of bovines (e.g. cows), ovines (e.g. sheep), caprines (e.g. goats), poultry (e.g. chickens, broilers, hens, turkeys, ducks, geese), swine (e.g. pigs), equines (e.g. ponies, horses, foals), lagomorphs (e.g. rabbits, hares), fishes (e.g. salmons, trouts) and other aquaculture species (e.g. shrimps).

The process as described above is useful for identifying the presence or absence of a stress state and/or for assessing (and/or for quantifying) the stress response level, wherein said stress state results from the submission of a subject to a stressor or challenge of any type. Preferably, said stress state includes an oxidative stress component. More preferably, said stress state results from the submission of a subject to:

a nutritional challenge (e.g. unbalanced diet in protein or energy level, diet contaminated with xenobiotics like mycotoxins or other contaminants, diet rich in antinutritional factors, diet rich in oxidized fat, diet rich in fiber . . . ), that can induce an inflammatory response or a disease, an environmental conditions challenge (e.g. thermic challenge, high relative humidity, high carbon dioxide level, wet litter . . . ), that can induce an inflammatory response or a disease, a physical challenge (e.g. physical manipulation challenge to catch the animal and/or a stress induced by animal transport), that can induce an inflammatory response or a disease, and/or a sanitary challenge (e.g. due to the presence of a bacterial pathogen, virus or parasite), that can induce an inflammatory response or a disease.

The sample can be a biological sample of any type. In particular, said sample can be selected from the group consisting of muscle tissue (preferably from skeletal muscle tissue), breast tissue, liver tissue, adipose tissue, skin, lymphoid tissue, placental tissue, gastrointestinal tract tissue (e.g. ileum tissue), genital tract tissue, central nervous system tissue, spinal cord, ganglion of the trigeminal nerve, urine, feces, feathers, tears, sperm, seminal fluid, cerebrospinal fluid, expectorations, bronchoalveolar lavage fluid, gastric secretions, saliva, serum, plasma and blood. The sample can be fresh or archived (e.g. a frozen sample, a formalin-fixed sample or a fixed, paraffin-embedded sample). In particular, the biological sample can be a biological fluid, preferably chosen among blood, plasma, serum, saliva and urine. It can also be any type of cells extracted from a blood sample, such as peripheral blood mononuclear cells (PMC), subpopulations of B cells, purified monocytes or neutrophils.

The detection and/or quantification of gene expression can be carried out at the mRNA level or at the protein level, by methods which are well-known to the person skilled in the art. Preferably, multiplex techniques are used, which allow the detection and/or quantification of the expression of several genes simultaneously.

Methods to detect and/or quantify gene expression at the mRNA level can be performed directly on mRNA, or indirectly (e.g. after a step of converting mRNA into cDNA and/or an amplification step). All these methods involve as a first step the isolation of RNA (and more particularly, mRNA) from the sample, by methods well-known to the person skilled in the art (see for instance Ausubel et al. (1997), Current Protocols of Molecular Biology, John Wiley and Sons, Rupp and Locker (1987), Lab Invest. 56:A67, or De Andres et al. (1995), BioTechniques 18:42044). In particular, RNA isolation can be performed using purification kit, buffer set and protease from commercial manufacturers, such as Qiagen, according to the manufacturer's instructions. Methods to detect and/or quantify gene expression at the mRNA level have for instance been described in Kricka et al., Clinical Chemistry, 1999, n° 45(4), p. 453-458 and in Relier G. H. et al., DNA Probes, 2nd Ed., Stockton Press, 1993, sections 5 and 6, p. 173-249, and include:

Amplification methods, which allow to generate multiple copies of a target nucleotide fragment, by the action of enzyme(s). Such amplification methods are well-known to the person skilled in the art and include PCR (Polymerase Chain Reaction), Fluidigm BioMark™ system, LCR (Ligase Chain Reaction; see, e.g., U.S. Pat. No. 5,494,810), RCR (Repair Chain Reaction), 3SR (Self Sustained Sequence Replication) with the patent application WO-A-90/06995, NASBA (Nucleic Acid Sequence-Based Amplification), TMA (Transcription Mediated Amplification) with the U.S. Pat. No. 5,399,491, and LAMP (Loop mediated isothermal amplification) with the U.S. Pat. No. 6,410,278. In particular, when the amplification method used is PCR, RT-PCR (reverse transcription PCR, which involves a step of retro-transcribing mRNA into cDNA) will more particularly be used, and more preferably, RT-qPCR (quantitative RT-PCR);

Hybridization methods, and in particular microarray methods, NanoString nCounter® system, Northern blot or in situ hybridization methods, such as FISH (Parker & Barnes (1999), Methods in Molecular Biology 106: 247-283), and Sequencing methods (and in particular, high-throughput sequencing methods).

Examples of methods for the detection and/or quantification of gene expression at the protein level can be selected among ELISA, Western blot, immunohistochemistry, flow cytometry and proteomics. The term "proteome" is defined as the totality of the proteins present in a sample at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2D PAGE); (2) identification of the individual proteins recovered from the gel, e.g. by mass spectrometry or N-terminal sequencing, and (3) analysis of the data using bioinformatics.

It is particularly advantageous to detect and/or quantify expression of extracellular proteins, which are secreted and can be detected non-invasively, for instance in blood, plasma, serum, urine or feather. It is more particularly useful to select proteins found in the extracellular matrix, such as proteins encoded by the following genes: Anxa1, Anxa2, Col1a1, Col12a1, Col14a1, Efemp1, Kera, Lgals1, Mgp, Nes, Postn, Slit3, Thbs1 and Tnc; more preferably proteins encoded by the following genes: Anxa1, Anxa2, Efemp1, Kera, Lgals1, Mgp, Nes, Postn, Slit3, Thbs1 and Tnc. It is even more particularly useful to select proteins which have already been detected in blood or urine, according to the literature, such as proteins encoded by the following genes: Anxa2, Efemp1, Lgals1, Mgp, Postn, Slit3 and Thbs1.

Preferably, the present invention relates to an in vitro process as described above, comprising a step of comparing gene expression level in said sample of said subject (test sample), for each of the at least four, at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six genes described above, with a reference value or with gene expression level in a reference sample. More preferably, said reference value corresponds to a control value or said reference sample corresponds to a sample from a control subject (i.e. a subject not submitted to a stressor), and a statistically-significant different gene expression level between the test sample and the reference value or the gene expression level in the reference sample, is indicative of a stress state in the subject.

A large number of algorithms can be used for data analysis, which are well-known to the person skilled in the art. An example of such an algorithm is the scoring based classification system described in Example 4. Other non-limiting examples of algorithms include structural and syntactic statistical classification algorithms, and methods of risk index construction, utilizing pattern recognition features, including established techniques such as, Principal Component Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shruken Centroids (SC), Kth-Nearest Neighbor, Boosting, Decision Trees, Neural Networks, Bayesian Networks, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, among others.

Individuals, wherein a stress state and/or a high level of stress response has been identified, can advantageously receive intervention solutions. Therefore, the process as described above can also comprise a step of providing said individual with an intervention solution, which is preferably a nutrition solution, more preferably selected from the group consisting of antioxidants, and in particular vitamins (e.g. vitamin E), aminoacids (e.g. methionine, selenomethionine), trace elements and probiotics.

The present invention also relates to an in vitro process for predicting the efficacy of an intervention solution in a subject, for monitoring the efficacy of an intervention solution in a subject and/or for identifying an intervention solution for a subject, comprising a step of detecting the expression and/or quantifying the expression level, in a sample of said subject, of at least four, at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc.

In particular, the present invention also relates to an in vitro process for predicting the efficacy of an intervention solution in a subject, comprising a step of detecting the expression and/or quantifying the expression level, in a sample of said subject, of at least four genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc. Preferred embodiments are the same as those described previously.

The present invention also relates to an in vitro process for monitoring the efficacy of an intervention solution in a subject, comprising a step of detecting the expression and/or quantifying the expression level, in a sample of said subject, after said subject has received the intervention solution, of at least four genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc. Preferred embodiments are the same as those described previously.

The present invention is also useful to screen candidate intervention solutions, to find new or optimal intervention solutions. Therefore, the present invention also relates to an in vitro process for identifying an intervention solution, comprising a step of providing a subject with a candidate intervention solution, and a step of comparing the expression and/or the expression level, between samples of said subject before and after said subject has received the candidate intervention solution, of at least four genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc. Preferred embodiments are the same as those described previously.

The present invention also relates to a kit comprising means for amplifying and/or detecting the expression of at least four, at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc. Preferred embodiments (in particular, preferred lists of genes) are the same as those described previously.

Preferably, said kit comprises means for amplifying and/or detecting the expression of a maximum of 200, 150, 100, 90, 80, 70, 60, 50, 40, 30, 29, 28, 27, 26, 25, 24, 23, 22, 21, 20, 19, 18, 17, 16, 15, 14, 13, 12, 11, 10, 9, 8, 7, 6, 5, 4 genes, in total (including target genes and possibly also, housekeeping genes). Indeed, said kit may comprise means for amplifying and/or detecting the expression, not only of genes selected from the list of twenty-six genes as described above, but also of other genes of interest (altogether, "target genes") and/or housekeeping genes.

Means for amplifying are well-known to the person skilled in the art and include for instance primers useful to perform a PCR reaction. A primer is a nucleotide fragment (usually between 5 and 100 nucleotides, preferably between 15 and 30 nucleotides), which can specifically hybridize with a part of a target nucleotide sequence and can act as a point of initiation of synthesis under specific conditions (e. g. in the presence of nucleotides and a DNA polymerase or the like, and at a suitable temperature and pH). In the present invention, a target nucleotide sequence would be a nucleotide fragment comprised within the mRNA or cDNA of a gene according to the present invention. Generally, primer pairs (consisting of two primers) are used.

A kit for PCR may also comprise other reagents useful to perform a PCR reaction, in particular a RT-PCR reaction, such as reverse transcriptases, polymerases (e.g. Taq polymerase), nucleotides, buffers and probes (see below).

Means for detecting gene expression are also well-known to the person skilled in the art and include:

means for detecting gene expression at the mRNA level, such as probes. Probes are fragments of DNA or RNA of variable length (usually between 5 and 500 nucleotides long), which can specifically hybridize with a part of a target nucleotide sequence under specific conditions, and which are labelled with a detectable tag (such as a fluorescent, a radioactive, an enzymatic tag or any other detection system), thereby allowing the detection of the target nucleotide sequence. In the present invention, a target nucleotide sequence would be a nucleotide fragment comprised within the mRNA or cDNA of a gene according to the present invention;

means for detecting gene expression at the protein level, such as antibodies and other types of binding molecules or binders (e.g. antibody fragments such as Fab, scFv, or affibodies, nanobodies, DARPins, anticalins—see Vazquez-Lombardi et al (2015), Drug Discovery Today, 20(10), p. 1271-1283, for instance).

The present invention further relates to the use of means for amplifying and/or detecting the expression of at least four, at least five, at least six, at least seven, at least eight, at least nine, at least ten, at least eleven, et least twelve, at least thirteen, at least fourteen, at least fifteen, at least sixteen, at least seventeen, at least eighteen, at least nineteen, at least twenty, at least twenty-one, at least twenty-two, at least twenty-three, at least twenty-four, at least twenty-five, at least twenty-six genes selected from the group consisting of Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc, or of a kit as described above, for identifying the presence or absence of a stress state, and/or for assessing (and/or for quantifying) the stress response level and/or for predicting the efficacy of an intervention solution and/or for monitoring the efficacy of an intervention solution in a subject, and/or for identifying or comparing an intervention solution. Preferred embodiments (in particular, preferred lists of genes) are the same as those described previously.

EXAMPLES

Figure 1A:
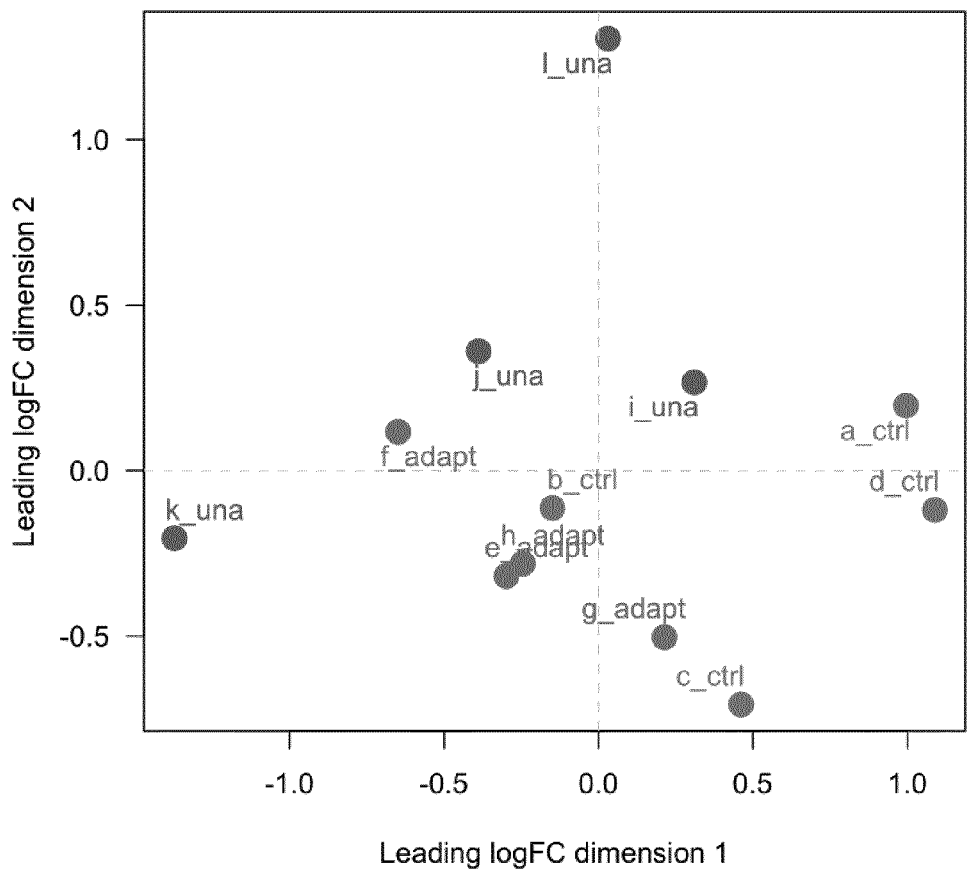
FIG. 1: Multi-dimensional scaling (MDS) plot of the different samples analyzed for each stress model: (A) chicken/nutrition-stress (PN model); (B) pigs/heat and inflammation-stress (CT model); (C) mice/physical exercise-stress (SN model) and (D) chicken/heat-stress (PT model). Dots correspond to the control (ctrl), adapted (adapt) and non-adapted (una) animal groups.

The present invention is illustrated non-exhaustively by the following examples. These examples are intended for the purpose of illustration only and are not intended to limit the scope of the present invention.

Example 1: Identification of Twenty-Six Conserved Genes Useful to Identify a Stress State in a Subject Material and Methods
Stress Model Design Four animal stress models were selected and designed based on previous studies, wherein three different species were submitted to four different stressors: (i) Chickens submitted to heat challenge (Loyau et al. (2016) BMC Genomics, 17: 329); (ii) Pigs submitted to heat and inflammatory challenges (Campos et al. (2014), The Veterinary Journal, 200, 404-409); (iii) Chickens submitted to nutritional challenge; (iv) Mice submitted to physical exercise challenge (Rederstorff et al. (2011), PLoS ONE, 6(8): e23094).

Briefly, in the chicken/heat-stress model (PT model), eggs were maintained either at 37.8° C. and 56% relative humidity during the whole incubation period or incubated at 39.5° C. and 65% relative humidity for 12 h/24 from embryonic day E7 to E16 included. After hatching, male chicks were transferred to a single poultry house and reared from day 0 to day 32. The temperature was decreased from 33° C. at day 0 to 21° C. at day 25 and maintained at 21° C. thereafter. On day 34, control or thermal manipulated chicken groups were exposed to 32° C. for 5 h. Animals without heat-challenge during embryogenesis and reared under standard conditions were used as controls. Body temperatures were measured during the heat challenge and on day 35 after return at 21° C. For the gene expression analysis, animals better tolerating heat by means of embryo heat acclimation were selected for low body temperature (adapted group) compared to the non-adapted and control groups that presented higher body temperature. They were slaughtered and breast muscles were recovered, snap-frozen and maintained at −80° C. until further analysis.

Concerning the pigs/heat and inflammation model (CT model), 77-day old pigs were kept constantly at 24° C. during a 14-day adaptation period, then divided into two groups, wherein animals were either maintained in thermo-neutral condition (24° C.) or exposed to high temperature for 17 days. For the high-temperature group, the room was kept at 24° C. during 5 days, then gradually increased to 30° C. Starting day 8 of the heat challenge period, pigs were administrated five injections of LPS from *E. coli* on days 8, 10, 12, 14, 16 of the heat stress period. Pigs were weighted individually at the beginning and at the end of the experimental period and rectal temperature was recorded. All animals were euthanized 24 hours after the final LPS injection. For the gene expression analysis, stressed animals presenting the largest weight deviation compared to controls were assigned to the non-adapted group, and animals exposed to the experimental treatment but with body weight similar to controls were assigned to the adapted group. Qualification into these two stressor-exposed groups was further validated based on plasmatic analyses evaluating hormonal response and oxidative stress status.

The chicken/nutrition-stress model (PN model) consisted in chickens fed with two different diets supplying low (17%) or usual (22%) crude protein levels. Birds were put on standard corn-soybean based starter diet (22% CP/3000 Kcal/kg) during the two first weeks of life to assure normal development. At day 15, chicken were treated with low or usual protein iso-energetic diet until 6 weeks old. For each condition and for 24 birds per treatments, blood and tissues samples were collected. Plasmatic corticosterol, iodotyronine T3-T4, TBA-RS and glutathione status were measured to evaluate the hormonal and oxidative status difference between dietary treatments during growth. In addition, animals weight was recorded before and after treatment. Based on gain of weight and oxidative parameters, the responses of stressed animals were highly variable, some of them closer to control reference values, the other one significantly divergent. To take into account this variability we defined two subgroups of stressed animals: adapted animals (feed conversion ratio similar to those of control animals) and non-adapted animals (feed conversion ratio significantly different to control animals). Breast muscle samples were collected at week 6 and stored at −80° C. until further analysis.

For the mouse/physical exercise-stress model (SN model), 8 to 12 months old transgenic Selenon−/− (KO/KO) mice or heterozygotes (KO/WT) mice were submitted to a forced swimming test. In this study, 15 KO/KO and 9 KO/WT mice were set to swim for six minutes each day during two months. Based on their ability to swim and body weight parameters, two subgroups were defined in the KO/KO cohort. The ones showing weight loss and difficulties to complete the swimming exercise were categorized as non-adapted animals, and the ones showing only subtle or no phenotypic alterations were categorized as adapted animals. Blood samples were collected and total oxidation-reduction potential capacity of the plasma was measured using the RedoxSYS® system (Luoxis, Englewood, USA). The values obtained for the stressed animals of both adapted and non-adapted subgroups compared to the KO/WT were in agreement with the loss of weight parameter. At the end of the two-month experimental period, animals were euthanized, paravertebral muscle tissues were collected and stored at −80° C. until further analysis.
Total RNA Extraction and Purification According to the biological indicators measured in each stress model, we determined four animals representative of the adapted and non-adapted subgroups; four animals of the control group were selected as well. Using a FastPrep-24 5GTM (Mpbio®) and 1.4 mm ceramic beads (6913-100, Mpbio®), muscle samples were homogenized in Tri Reagent buffer (Sigma®) at 1.5 ml per 100 mg tissue, twice for 40 sec at 6 m/s speed. After centrifugation for 10 min at 12,000 g at 4° C., 1 mL of supernatant was collected. Two hundred μL chloroform was added and after vortexing, the mix was centrifuged for 10 min at 12,000 g at 4° C. Five hundred μL of the upper aqueous phase was collected and RNAs were precipitated by addition of one volume isopropanol 100% at room temperature for 10 min. After centrifugation for 10 min at 10,000 g at 4° C., supernatant was removed and the pellet was dried at room temperature for 10 min. The RNA pellet was resolubilized in 50 µL of RNase-DNase free water and incubated for 10 min on ice. RNA concentration was determined using a NanoDrop 1000 spectrophotometer (Thermo Scientific).

Total RNAs, including mRNAs and long-non coding RNAs were then purified, using the RNA Clean & Concentrator™-5 kit (Zymo Research). Ten µg total RNA were purified according to manufacturer's instructions. The concentration and the purity of the RNA samples were measured using a NanoDrop, and their integrity (RIN) was evaluated using a Bio-Analyzer 2100 (Agilent Technologies). The RIN values ranged from 8.0 to 9.6.

RNA Sequencing

Purified RNAs were reverse-transcribed into cDNAs and sequencing was conducted at the GenomEast Plateforme, IGBMC using the HiSeq Illumina® technology (HiSEQ 4000). FASTQ sequence files containing reads were retrieved.

RNA-Seq Data Processing

HISAT2 tool version 2.0.4 with default parameters was used to perform alignment of reads against the genomes, according to genome annotations. The GTF annotations and FASTA genome files used in this step were as followed: (i) For chickens, Galgal5 genome with its associated NCBI annotations; (ii) For pigs, Sscrofa11.1 genome with its associated NCBI annotations and (iii) for mice, GRCm38.p5 (mm10.p5) genome with its associated Ensembl version M14 annotations.

Gene expression level was measured by reads counting using the HTSeq tool version 0.6.1 using default parameters. Finally, the EdgeR tool of the SARTools R package was used to define differentially expressed genes between the three tested conditions: adapted versus control, non-adapted versus control and non-adapted versus adapted, respectively referred as AvsC, NAvsC and NAvsA. To manage samples variability, we used a modified version of the EdgeR robust mode, which performs a different dispersion calculation according to the method developed by Zhou and Robinson (ref biblio). The same parameters were used for all models, applying the default Benjamini-Hochberg p-value adjustment method. Differentially expressed (DE) genes from each model were defined using a classical threshold for the adjusted p-value (padj) of 0.05.

Model Comparisons

Once a list of DE genes was established for each model, we searched the human orthologous name of each of these genes using the BioMart tool accessible online from the Ensembl website (ensembl.org). This step let us deal with inter-species nomenclature heterogeneity. We then merged all DE genes of each comparison in each model and compared the four lists to characterize conserved genes involved in the stress response. We defined the conserved genes list by selecting all genes in common between at least three of our four models. This choice was made to be more permissive, comparing four strictly different models, and to avoid mis-assignment biases during the BioMart step mainly because of gene families composed of a large number and highly similar paralogous genes.

Results

Previous analyses defined for each model a set of physiological indicators (weight loss, blood hormone markers, measurements of oxidative level) characteristic of stressed animals compared to controls. In our experiments, analyses of these markers indicated that the responses of stressed animals were highly variable (non-unimodal distribution), some of them closer to control reference values, and the other ones significantly different. To take into account this dispersity among the stressed animals, we defined two subgroups: the adapted and the non-adapted animals, with parameters convergent or significantly different from control animals respectively. For each group—adapted, non-adapted and control—a set of four animals was selected. Transcriptomic analyses were conducted in muscle, a dynamic tissue highly responsive to stressor exposure. Total RNA was extracted from muscle samples and RNA transcripts were sequenced using RNAseq technology. Quality of data acquisition was validated using FASTQC. SARTool was used to evaluate the data dispersion and the normalization procedure of the gene expression for each sample. A MDS plot representation verified the relative clustered distribution of the analyzed animals into the three identified groups—control, adapted and non-adapted, for each model (FIG. 1), despite their large inter-individual variability. However, for the chicken/heat-stress model, one of the four control samples (a_ctrl) showed an atypical variability compared to other animals of his group (FIG. 1D), and therefore was considered as an out-layer and removed from the control set for the gene expression comparative analysis.

Figure 1B:
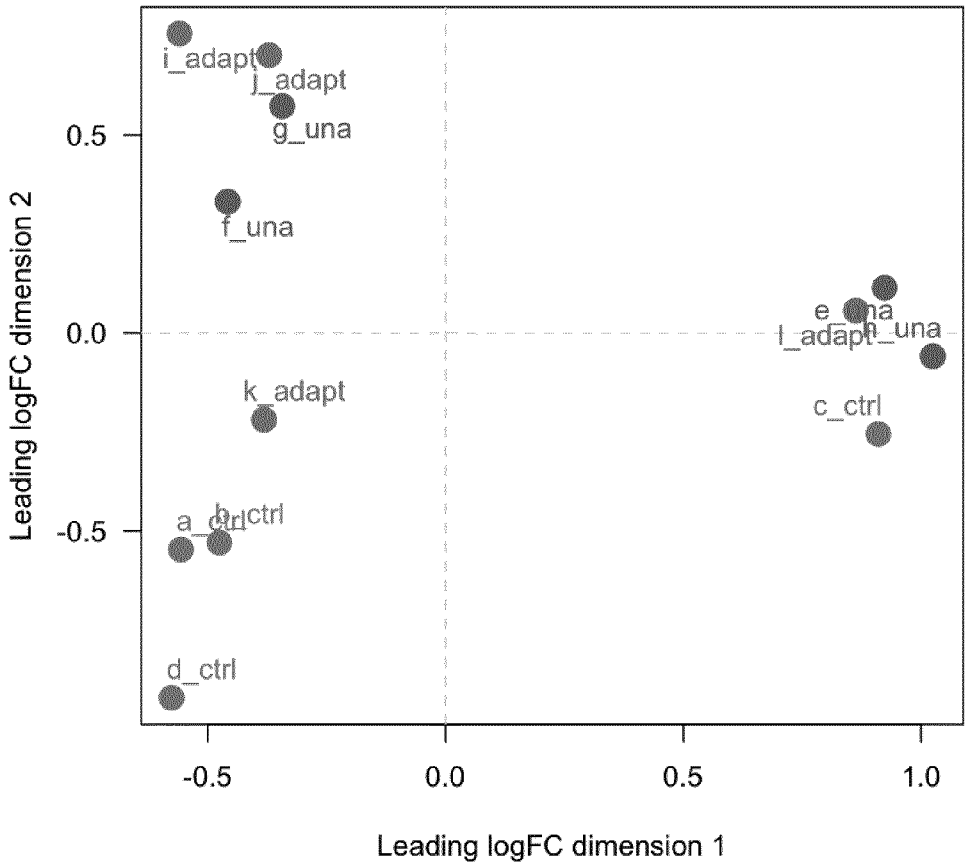
Figure 1C:
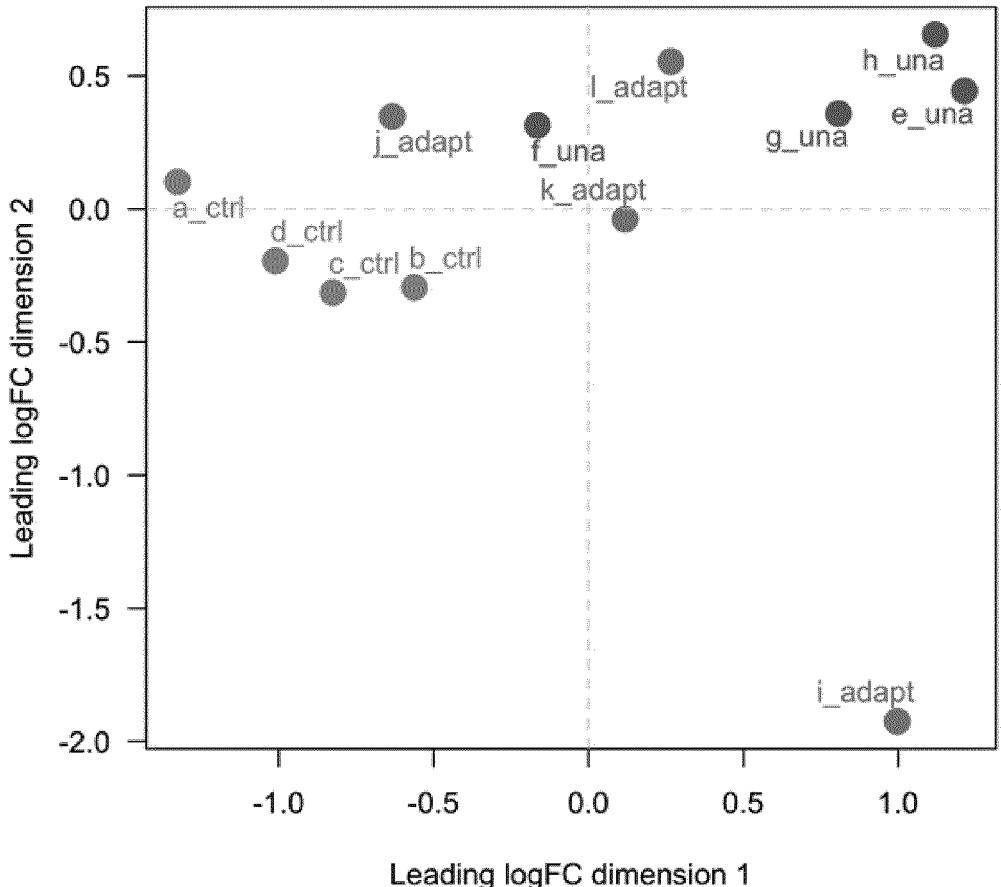
Figure 1D:
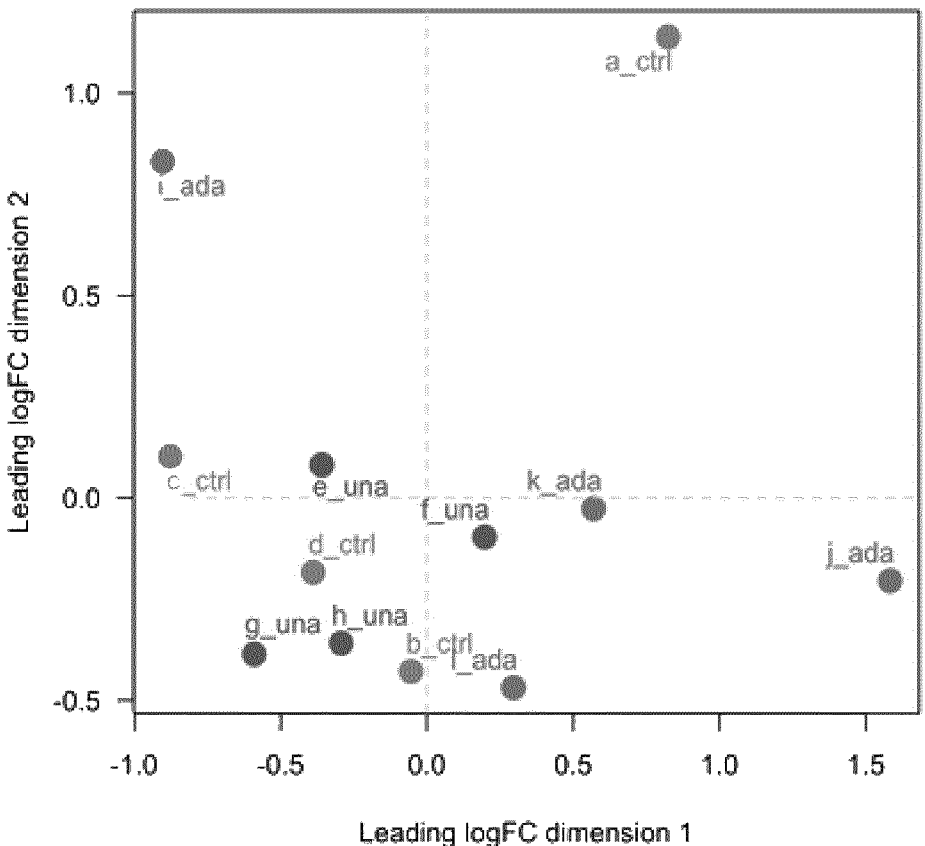

For the pigs/heat and inflammation-stress model, we noticed an unusual clustering of the animals into two groups, independently of the stress context, that could be attributed to sex differences mainly (FIG. 1B: animals clustered on the left side corresponded to females except j-adapt, and animals grouped on the right side corresponded to males). Therefore, a blocking factor "sex" was introduced for the comparative gene expression analysis to take into account the stress response differences between male and female pigs. Comparative analysis between the three categories of stressed and control animals identified a list of differentially expressed (DE) genes in each stress model. Number of DE genes between the stressed and control animals is reported in Table 1. Remarkably, the comparison of non-adapted versus control showed the highest number of DE genes in most cases, but in one model (the chicken/heat-stress model). This observation suggested that non-adapted animals are more divergent from control animals than the adapted ones, based on the expression of their genomic program. This is not the case for the chicken/heat-stress model, but in this case animals were exposed to a pretreatment during embryogenesis that induced pre-adapted, inducing the setting of a genomic program that stimulate adaptation.

TABLE 1

Number of DE genes per comparison for each model, with a padj threshold of 0.05.

| Models Comparison | Pig/heat and inflammation-stress model | Mice/physical exercise-stress model | Chicken/heat-stress model | Chicken/nutrition-stress model |
|---|---|---|---|---|
| AvsC | 282 | 356 | 278 | 65 |
| NAvsC | 339 | 1394 | 39 | 275 |
| NAvsA | 35 | 220 | 133 | 15 |

AvsC: adapted versus Control; NAvsC: non adapted versus Control; NAvsA: non adapted versus adapted.

Figure 2:
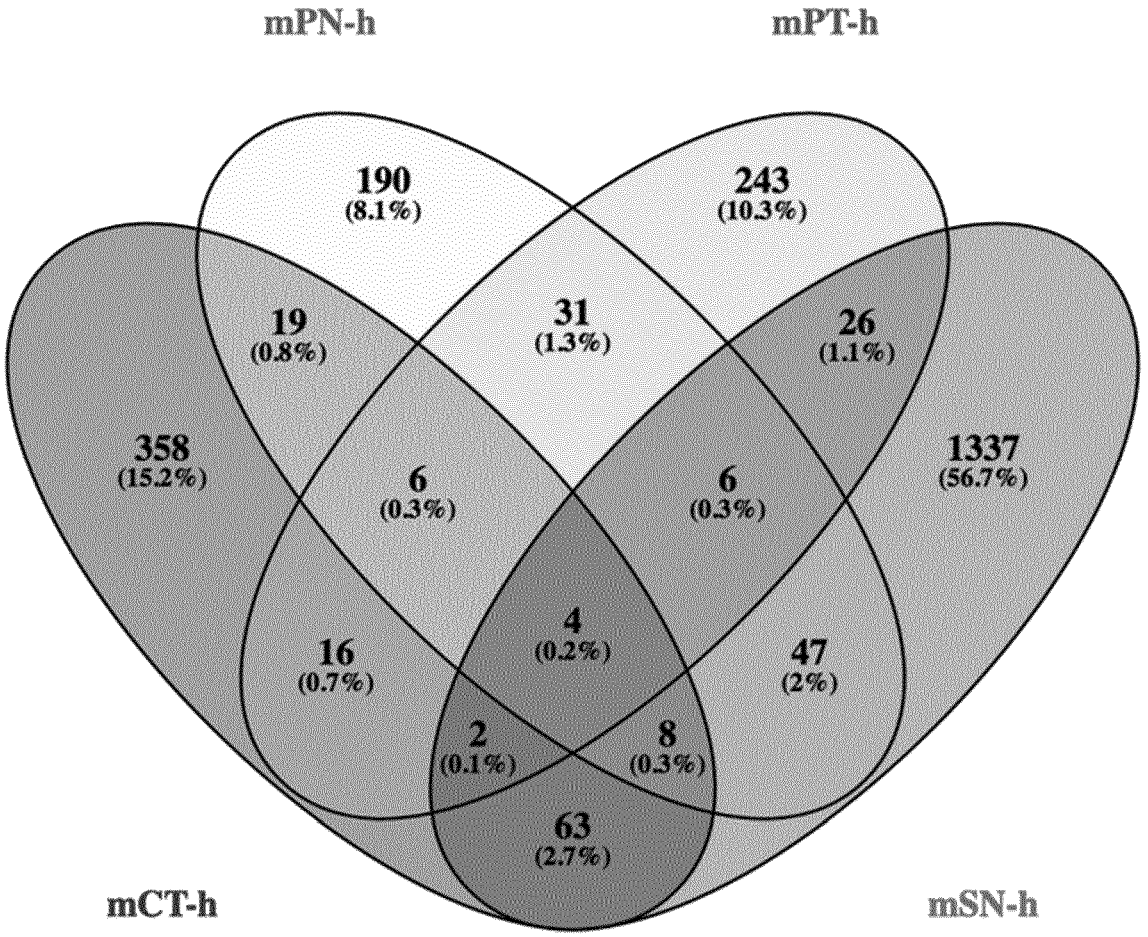
FIG. 2: Venn diagram of all differentially-expressed (DE) genes in the four stress models. This representation shows that four genes are differentially expressed in at least one comparison for each model. This list was extended to 26 genes by considering genes conserved in at least three of the four models. mPN-h (mRNA genes from the PN model using the human gene nomenclature), mPT-h (mRNA genes from the PT model using the human gene nomenclature), mCT-h (mRNA genes from the CT model using the human gene nomenclature), mSN-h (mRNA genes from the SN model using the human gene nomenclature). This diagram was generated using the Venny 2.1.0 website tool (bioinfogp.cnb.csic.es/tools/venny). P

The differential expression analysis let us define a list of DE genes based on the chosen padj threshold of 0.05. The number of DE genes found with this filter for each comparison of each model is summarized in Table 1. To compare these lists together, we first created one list of DE gene per model, no matter in which comparison they were differentially expressed, assuming that it will always be due to stress response. Then we used a Venn diagram representation and found four genes conserved between our four models (FIG. 2). In order to minimize biases in this approach, we chose to extend the list to genes conserved between at least three of our models, and we then found 26 conserved genes differentially expressed during the stress response process: Ankrd33b, Anxa1, Anxa2, Chac1, Cidea, Col1a1, Col12a1, Col14a1, Efemp1, G0s2, Gfpt2, Hmox1, Kctd12, Kera, Lgals1, Mgp, Mrc1, Nes, Panx1, Postn, Runx1, Serpinh1, Sh2b2, Slit3, Thbs1 and Tnc (Table 2).

The four genes conserved between the four models were: Anxa1, Anxa2, Chac1 and Postn. The six genes conserved between the PT, PN and CT models were: Col1a1, Col12a1, Gfpt2, Mgp, Thbs1 and Tnc. The two genes conserved between the PT, SN and CT models were Mrc1 and Serpinh1. The six genes conserved between the PT, PN and SN models were: Cidea, Hmox1, Kctd12, Lgals1, Sh2b2 and Slit3. The eight genes conserved between the CT, PN and SN models were: Ankrd33b, Col14a1, Efemp1, G0s2, Kera, Nes, Panx1 and Runx1.

To edit the graphical properties of the String representation, we also used the Cytoscape software version 3.6.1. This tool allowed us to color nodes with a grey gradient according to their log2 fold-change, giving more information in terms of differential expression level. In order to obtain more information about the function of these genes, we performed enrichment analyses using again the String website providing the user with GO-terms statistical enrichment analyses in addition to network representation.

Results

Figure 3:
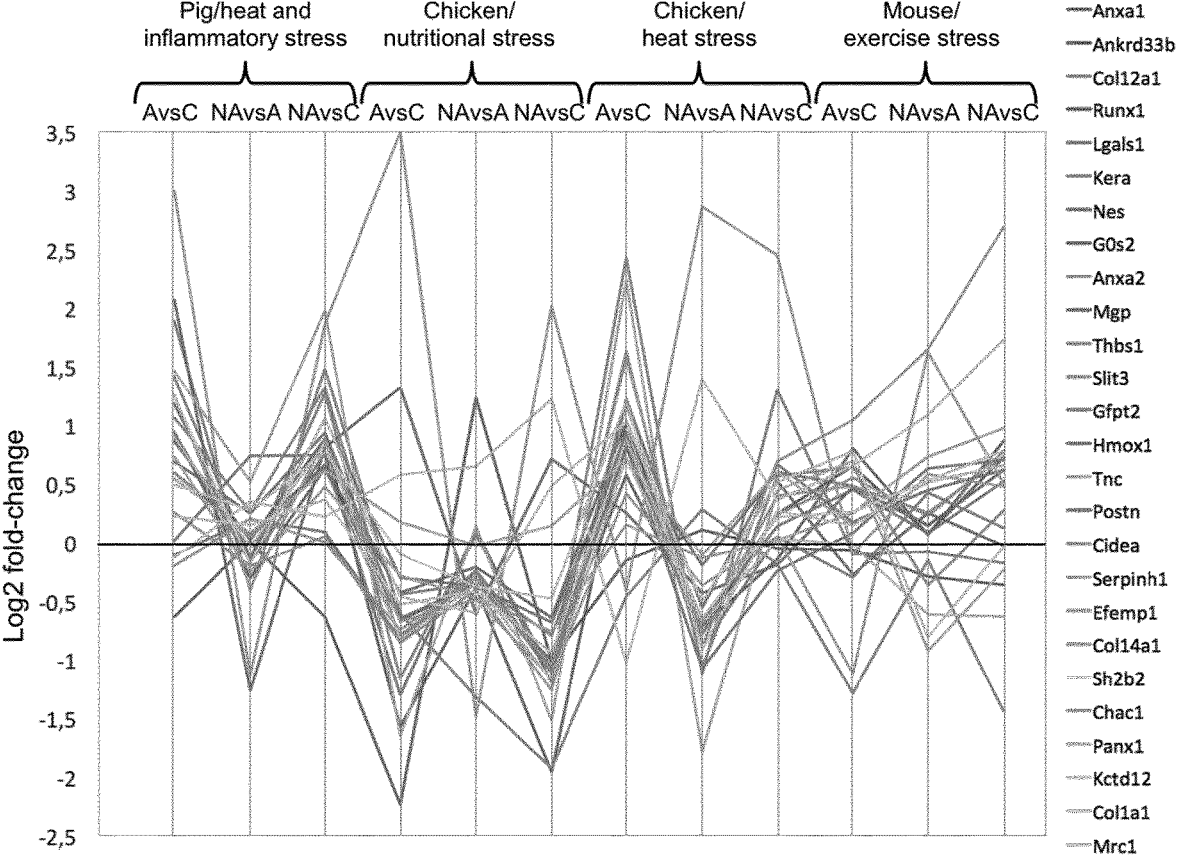
FIG. 3: Differential expression profile for each of the 26 conserved genes in each comparison for the four models. Each vertical line represents the variation of gene expression, expressed as log 2 of fold-change, between two conditions: adapted versus control (AvsC), non-adapted versus control (NAvsC) and non-adapted versus adapted (NAvsA). The black solid line indicates the null log 2 fold-change level corresponding to no differential expression. It was observed that most of the genes displayed a convergent expression profile across comparisons and models.

To better characterize the biological function of the 26 conserved genes, we first used a parallel coordinates visualisation to compare their expression profile in each model using their log 2 fold-change values (FIG. 3). This representation showed that even if the differential expression level of those genes was not the same between the four models, most of them shared the same expression profile across stress models being almost always up-regulated or down-regulated together. The most divergent gene compared to this overall trait was Chac1. This observation

TABLE 2

List of differentially expressed genes conserved between different models.

| Gene | NM reference sequence in human (mRNA) | NP reference sequence in human (protein) | Identified function of the protein | Cell localization of the protein |
|---|---|---|---|---|
| Ankrd33b | NM_001164440 | NP_001157912 | Unknown | Unknown |
| Annexin A1-Anxa1 | NM_000700 | NP_000691 | Cell membrane reparation and inflammation | Memb, secreted, nucleus, cyto |
| Annexin A2-Anxa2 | NM_001002858.2 | NP_001002858.1 | Cell membrane reparation | Secreted |
| Chac1 | NM_024111.6 | NP_077016.3 | Glutathion degradation | Cyto |
| Cidea | NM_001318383.1 | NP_001305312.1 | Apoptosis, energy metabolism | Nucleus, lipid droplets |
| Collagen 1-Col1a1 | NM_000088 | NP_000079 | ECM component | ECM |
| Collagen 12-Col12a1 | NM_004370.6 | NP_004361.3 | ECM component, fibril associated collagen | ECM |
| Collagen 14-Col14a1 | NM_021110 | NP_066933 | ECM component, fibril associated collagen | ECM |
| Fibulin 3-Efemp1 | NM_001039348.3 | NP_001034437.1 | Cell adhesion and differentiation | ECM |
| G0s2 | NM_015714 | NP_056529 | Lipolysis and apoptosis control | Mitochondria |
| Gfpt2 | NM_005101 | NP_005101 | glutamine-fructose-6-phosphate transaminase 2 | Cyto |
| Hmox1 | NM_002133 | NP_002124 | Heme oxygenase, forms biliverdin | ER |
| Kctd12 | NM_138444 | NP_612453 | Auxiliary subunit GABA-B receptors | Memb |
| Kera | NM_007035 | NP_008966 | Keratan sulfate proteoglycane | ECM |
| Lgals1 | NM_002305 | NP_002296 | Lectin binding galactoside, role in apotosis, adhesion and cell differentiation | ECM |
| Mgp | NM_000900 | NP_000891 | Calcium mineralization control | ECM |
| Mrc1 | NM_002438 | NP_002429 | Macrophage mannose receptor | Memb |
| Nes | NM_006617 | NP_006608 | Vimentin intermediate filaments assembly dynamics | ECM, cytoskeleton, cyto |
| Pannexin 1-Panx1 | NM_015368 | NP_056183 | Structural component of gap junctions | Memb, ER |
| Periostin-Postn | NM_006475.3 | NP_006466.2 | Cell adhesion | Secreted, ECM |
| Runx1 | NM_001754.4 | NP_001745.2 | Transcription factor important for muscle regeneration | Nucleus |
| Serpinh1 | NM_001207014.1 | NP_001193943.1 | Collagen chaperone | ER |
| Sh2b2 | NM_020979.4 | NP_066189.3 | Adapter protein for tyrosine kinase receptors, insulin response | Memb, Cyto |
| Slit3 | NM_001271946.1 | NP_001258875.1 | Cellular migration | ECM |
| Thbs1 | NM_003246 | NP_003237 | Adhesive glycoprotein, heparin and collagen binding | ECM, ER |
| Tenascin-Tnc | NM_002160 | NP_002151 | Cell adhesion and growth | ECM |

ECM = Extra Cellular Matrix; ER = Endoplasmic reticulum; Cyto = cytoplasm; Memb = membrane Example 2: Functional Characterization of the Twenty-Six Conserved Genes After having obtained the list of the 26 conserved genes, we wanted to know if they play a role in the same biological process, if they are co-localised and if they could interact together.

Materials and Methods

To investigate the connectivity degree of our genes of interest we used the String 10.5 website (string-db.org). Edges correspond here to predicted functional associations.

indicates that a major part of these genes are co-expressed, possibly by a unique signalling pathway or transcription factor. We could also propose that these co-expressed genes should be part of the same biological process, playing a functional role together.

We then characterized the cellular localization of the proteins encoded by these genes. Combining literature and Uniprot data, we could characterize a sub-list of 14 proteins out of 26 that can be localized outside of the cell in the extracellular matrix (ECM) or secreted (Table 2). A bibliographic investigation of these proteins also put in evidence that a part of them are members of the matricellular protein family. This family consists in extracellular proteins found in the ECM but not only involved in its structural architecture. Matricellular proteins are known to participate in several processes like regulation of cellular adhesion, differentiation and proliferation, cell-cell interactions and also signal transduction pathways.

Figure 4:
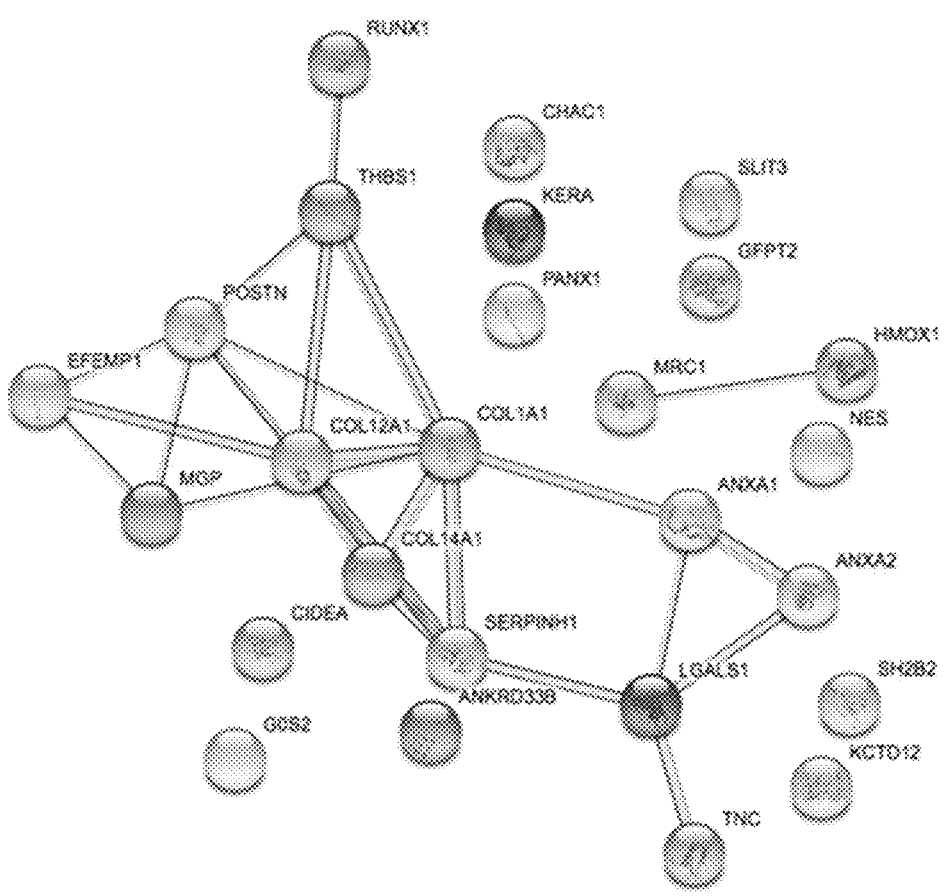
FIG. 4: String network representation of the 26 proteins encoded by the 26 conserved genes. Edges grey intensity represent the confidence degree for each interaction, with darker lines corresponding to higher confidence score. The statistical significance P-value obtained for this network was 3.21*e-10.

Using the String website, we showed that 15 of our 26 proteins of interest (13 in a network, and 2 others) are at least functionally connected, supporting the co-expression and co-localization evidences (FIG. 4). This connectivity suggests that these genes are involved in a common biological process.

Moreover, ontological enrichment using the String website were also in agreement with the concept of extracellular proteins playing a role in a common biological process, pointing out enriched terms, such as "extracellular matrix organization", "collagen fibril organization" or "regulation of signal transduction" (Table 3).

All these evidences put together indicate that a subset of the conserved 26 genes is related to a unique biological process occurring outside of the cell at the ECM level. We can also precise that this biological process is not only related to the structural composition of the ECM, but also involved in the cellular fate through cell-cell communication and intracellular signal transduction, in agreement with response to stress.

Example 3: GEO Database Investigation

The 26 genes identified in the present study are not part of the classical genes found in the majority of other stress state or stress response studies. To confirm their involvement in this biological process, we then analysed the GEO database (Gene 10 Expression Omnibus, ncbi.nlm.nih.gov/geo/) from the NCBI. This publicly available database contains raw data from RNA-seq and microarray experiments and can be queried online or by command-line requests.

Material and Methods

At the time we performed this search (February 2017), the GEO database contained about 95096 experiments. In order to query the GEO database with our gene list, we used a homemade Python script, which allowed us to query the GEO database for each of the 26 genes, and to retrieve all experiments in which at least one of these genes was differentially expressed. We then checked whether these genes were frequently differentially expressed in studies about what we defined stressors exposure.

Results

We found three experiments, each showing 11 differentially expressed genes out of our 26 genes (but not the same 11 genes in each of the three experiments), one of them about skeletal muscle response to a physical exercise, and the other ones related to cancer diseases investigations. When combining the genes found in the three experiments,

TABLE 3

Ontological enrichment in the "biological process" category according to the
String website. These data indicates that a majority of the 26 genes are involved in
extracellular functions such as extracellular matrix organization and/or regulation of
signal transduction.
Biological Process (GO)

| pathway ID | pathway description | count in gene set | false discovery rate |
|---|---|---|---|
| GO: 0030198 | extracellular matrix organization | 9 | 1.54e-06 |
| GO: 0030199 | collagen fibril organization | 5 | 4.94e-06 |
| GO: 0048731 | system development | 16 | 0.000473 |
| GO: 0001501 | skeletal system development | 7 | 0.00182 |
| GO: 0010033 | response to organic substance | 13 | 0.00182 |
| GO: 0007275 | multicellular organismal development | 16 | 0.00191 |
| GO: 0014070 | response to organic cyclic compound | 8 | 0.00426 |
| GO: 0032963 | collagen metabolic process | 4 | 0.00442 |
| GO: 0009966 | regulation of signal transduction | 12 | 0.00458 |
| GO: 0051239 | regulation of multicellular organismal process | 12 | 0.00458 |
| GO: 0060351 | cartilage development involved in endochondral bone morphogenesis | 3 | 0.00458 |
| GO: 0051241 | negative regulation of multicellular organismal process | 8 | 0.00925 |
| GO: 1901700 | response to oxygen-containing compound | 9 | 0.00951 |
| GO: 0009611 | response to wounding | 7 | 0.0153 |
| GO: 0031340 | positive regulation of vesicle fusion | 2 | 0.0153 |
| GO: 0032964 | collagen biosynthetic process | 2 | 0.0153 |
| GO: 0048583 | regulation of response to stimulus | 13 | 0.0153 |
| GO: 0001817 | regulation of cytokine production | 6 | 0.0161 |
| GO: 0010812 | negative regulation of cell-substrate adhesion | 3 | 0.0197 |
| GO: 0051216 | cartilage development | 4 | 0.0202 |
| GO: 0048856 | anatomical structure development | 14 | 0.022 |
| GO: 0060348 | bone development | 4 | 0.0229 |
| GO: 0060350 | endochondral bone morphogenesis | 3 | 0.0264 |
| GO: 0000302 | response to reactive oxygen species | 4 | 0.0281 |
| GO: 0009653 | anatomical structure morphogenesis | 10 | 0.0281 |
| GO: 0048513 | organ development | 11 | 0.0367 |
| GO: 0030574 | collagen catabolic process | 3 | 0.0394 |
| GO: 0001818 | negative regulation of cytokine production | 4 | 0.0397 |
| GO: 0048545 | response to steroid hormone | 5 | 0.0397 |
| GO: 0051259 | protein oligomerization | 5 | 0.0397 |
| GO: 0061448 | connective tissue development | 4 | 0.0397 |
| GO: 0033555 | multicellular organismal response to stress | 3 | 0.0437 |
| GO: 0009719 | response to endogenous stimulus | 8 | 0.0449 |
| GO: 0048705 | skeletal system morphogenesis | 4 | 0.0449 | this provided the following list of genes: Anxa1, Anxa2, Col1a1, Col14a1, Efemp1, Hmox1, Lgals1, Mgp, Mrc1, Nes, Panx1, Postn, Runx1, Serpinh1, Slit3, Thbs1 and Tnc. In most of the cases, experiments that we identified using this method were related to stressors exposure, extracellular matrix-related diseases, or aging processes. These investigations also showed that only a subset of our 26 genes is involved in these mechanisms and that a part of them were more frequently differentially expressed together. These results suggest again that only a part of the initial set of genes is implicated in the evolutionary conserved stress response, and that the other ones are more dependent on the stress factor nature or are more specie-specific.

Example 4: Evaluation of the 4- to 26-Gene Signatures Derived from the Twenty-Six Genes, in Another Animal Model The performance of the various signatures derived from the twenty-six genes, for identifying the presence or absence of a stress state in a subject (as reflected by the "stress score"), and/or for assessing the stress response level in a subject, and in particular for qualifying the adaptation state in a subject (as reflected by the "adaptation score" and the "non-adaptation score"), was checked in the animals of the PN model under non-adaptation conditions (as described in Example 1) and also tested in another animal model of chicken exposed to a xenobiotic stress (induced by the oxidant molecule paraquat).

Material and Methods

Model of Chicken Exposed to Paraquat-Induced Stress ("Chicken-Paraquat Model")

All experimental procedures used in the current study were approved by the Ethics and Research Committee of the institution conducting the study. A total of 144 one-day-old Ross 308 male broiler chicks, with an average body weight (BW) of 39 g, were reared from D1 to D21. They were allocated in 72 battery cages (0.5×0.42 m²) with wire floors (6 chicks/cage) in environmentally controlled rooms. The birds were randomly assigned to treatment pens with similar starting weights. Each cage was equipped with one trough feeder and one drinker. Birds had ad libitum access to mash feeds and water during all study. Average temperature was 33° C. at placement, being reduced by 1° C. every 2 days until 23° C. to provide comfort throughout the study. The lighting program was 18 hours light and 6 hours dark during each 24 hours period throughout the trial.

The experimental design was a completely randomized factorial design, consisting of a placebo or oxidative stress groups thus two experimental treatments, and 12 replicates per treatment with 6 birds for each replicate. The oxidative stress was applied only from D7 to D14, through the supplementation of a xenobiotic, i.e. paraquat dichloride hydrate (Sigma-Aldrich Company Ltd., Dorset, UK), through the water supply system at the dose of 110 µg/mL. This dosage was achieved by using water containers, individually located in each cage. The control group received standard water (placebo) on the same period using similar containers. A starter and grower diets were provided from D1 to D7, and D8 to D21, respectively. The basal diets were standard wheat/corn-soy-based broiler diets, and were formulated to meet or exceed the nutrient requirements of broilers, as recommended by the NRC (1994). Body weight (BW) was recorded on D1, D7, D14 and D21. On D14 and D21, one bird per pen replicate of each treatment was sacrificed for tissue collection. Briefly, 100 mg of tissue (breast, liver and ileum) were immersed in 2-mL Eppendorf tubes containing 1 mL RNAlater® (Sigma-Aldrich), and kept at −20° C. until analysis. RNA extraction and purification was conducted as described in Example 1.

Measurement of Gene Expression Levels by Quantitative RT-PCR

To remove traces of contaminant genomic DNA, 2.5 µg of total RNA was treated with 2.5 U of DNaseI (ThermoFischer) in a final volume of 204 for 15 min at 25° C. Next, DNase was inhibited by addition of EDTA to a final concentration of 8 mM and incubated for 10 min at 70° C. Half of the DNase-treated RNA sample was reverse transcribed (RT), the other half was kept as no-RT control. RNA was denatured in a total volume of 17.6 µL containing 1.25 µg total RNA, 5 mM of nonanucleotide random primer (dN9) and 0.5 µM each dNTPs (Thermofischer). This mix was heated to 70° C. for 5 min in a thermocycler (SimpliAmp™, Life Technologies). Then, RT-AMV buffer (Life Sciences Advance Technology) was added together with 40 U RNAsine (Promega) and 0.25 U AMV Reverse Transcriptase (RT) (Life Sciences Advance Technology), and the volume was adjusted to 21.6 µL. Primers were hybridized by incubation at 25° C. for 15 min, and extension was conducted for 2 hours at 45° C. in thermocycler. No-RT controls were treated in parallel, but addition of AMV-RT enzyme was omitted.

For the quantitative PCR reaction, 1 µL of cDNA sample diluted to ⅓ was mixed to 2 µL specific primers mix 2.5 mM each and 5 µL of 2× Takyon sybrgreen—No ROX (Eurogentec) in a final volume of 10 µL. Each PCR reaction was set in triplicate. Amplification was conducted on a LC480 LightCycler® Nano (Roche) using 384 well plates and the following program: 1 initial activation cycle at 95° C. for 3 min, then 45 cycles [95° C. for 10 sec; 60° C. for 15 sec; 72° C. for 15 sec]. Specificity of each amplification was monitored by fusion curve technic detecting a single peak corresponding to one single amplicon, consisting in an initial denaturation at 95° C. for 5 sec, followed by ramping from 55 to 95° C. at 0.11° C./sec, and 5 acquisitions per sec. Ct were determined using a regression mode, only Ct exceeding 35 cycles were considered for further analyses, and differential expression level was calculated according to the ΔΔCT method.

Algorithmic Analysis and Radar Plot Representation

Scores for stress, adaptation and non-adaptation were determined based on the differential expression, between oxidative stress and placebo groups, of a list of genes and an algorithm, which integrates observations made on our four reference stress models. These scores were then plotted using an adequate representation for easy and intuitive diagnostic of animal stress status.

Determination of the Stress (S) Score

First, the differential expression (DE) of each of the 26 genes was encoded according to the technics used to measure the gene expression, as follows:

For RNA-seq analyses (as used in the four initial stress models, and in particular in the PN model under non-adaptation conditions, "PN-NA" model, which is assessed in this Example):

If up-regulated (fold-change, FC>1 and adjusted p-value0.05): variable=u

If down-regulated (FC<1 and adjusted p-value0.05): variable=d

If not DE (FC=1 or adjusted p-value>0.05): variable=- p-value was determined by EdgeR and adjusted using the Benjamini-Hochberg method.

For RT-qPCR analyses (as used in the chicken paraquat model):

If up-regulated (fold-change, FC>1.5): variable=u

If down-regulated (FC<0.6667): variable=d

If not DE (0.6667<FC<1.5): variable=-

Then, considering that MRC1, SERPINH1, GOS2 and CHAC1 genes (grouped under the list "ListA") were only observed up-regulated or not DE in stressed animals (adapted or non-adapted) and never DE in control animals:

ListA score=(Number of genes of List *A* with variable=*u*)

Considering that ANKRD33B gene ("ListB") was only observed down-regulated or not DE in stressed animals (adapted or non-adapted) and never DE in control animals:

ListB score=1, if ANKRD33B variable=*d*

ListB score=0, if ANKRD33B variable=*u* or -

Considering that each of the 21 remaining genes (referred to as "ListC") were observed up-regulated, down-regulated or not DE in stressed animals (adapted or non-adapted) and never DE in control animals:

ListC score=(Number of genes of List *C* with variable=*u*)+(Number of genes of List *C* with variable=*d*)

Finally, the stress score value was computed as:

Stress (*S*) score=(ListA score+ListB score+ListC score)/number of genes of the signature considered*100

Determination of the Adaptation (A) and Non-Adaptation (NA) Scores

In our four reference models (PN, PT, CT and SN models), 15 genes were found up- or down-regulated in non-adapted animals only, and 1 gene was found up- or down-regulated in adapted animals only.

Considering that COL1A1, PANX1, EFEMP1, CIDEA, TNC, GFPT2, SLIT3, THBS1, MGP, LGALS1, POSTN and ANXA2 genes (grouped under the list "ListD") were observed down-regulated in non-adapted animals only, and never in adapted nor control animals:

ListD score=(Number of genes of List *D* with variable=*d*)

Considering that SH2B2 gene ("ListE") was observed up-regulated in non-adapted animals only, and never in adapted nor control animals:

ListE score=1, if SH2B2variable=*u*

ListE score=0, if SH2B2 variable=*d* or -

Considering that KCTD12 and NES genes (grouped under the list "ListF") were found DE (up-regulated or down-regulated) in non-adapted animals only, and never in adapted animals:

ListF score=(Number of genes of List *F* with variable=*u*)+(Number of genes of List *F* with variable=*d*)

The non-adapted score value was computed as:

Non-adapted (*NA*) score=(ListD score+ListE score+ListF score)/number of genes of the signature which are up- or down-regulated in non-adapted animals only*100

Considering that SH2B2 gene ("ListG") was observed down-regulated in adapted animals only, and never in non-adapted nor control animals:

ListG score=1, if SH2B2variable=*d*

ListG score=0, if SH2B2 variable=*u* or -

The adapted score value was computed as:

Adapted (*A*) score=(ListG score)/number of genes of the signature which are up- or down-regulated in adapted animals only*100

Score Plotting

S, NA and A scores were plotted on three corresponding axes in the form of a radar plot. Numbers on the plot refer to the percentage of each score.

Results

Figure 5:
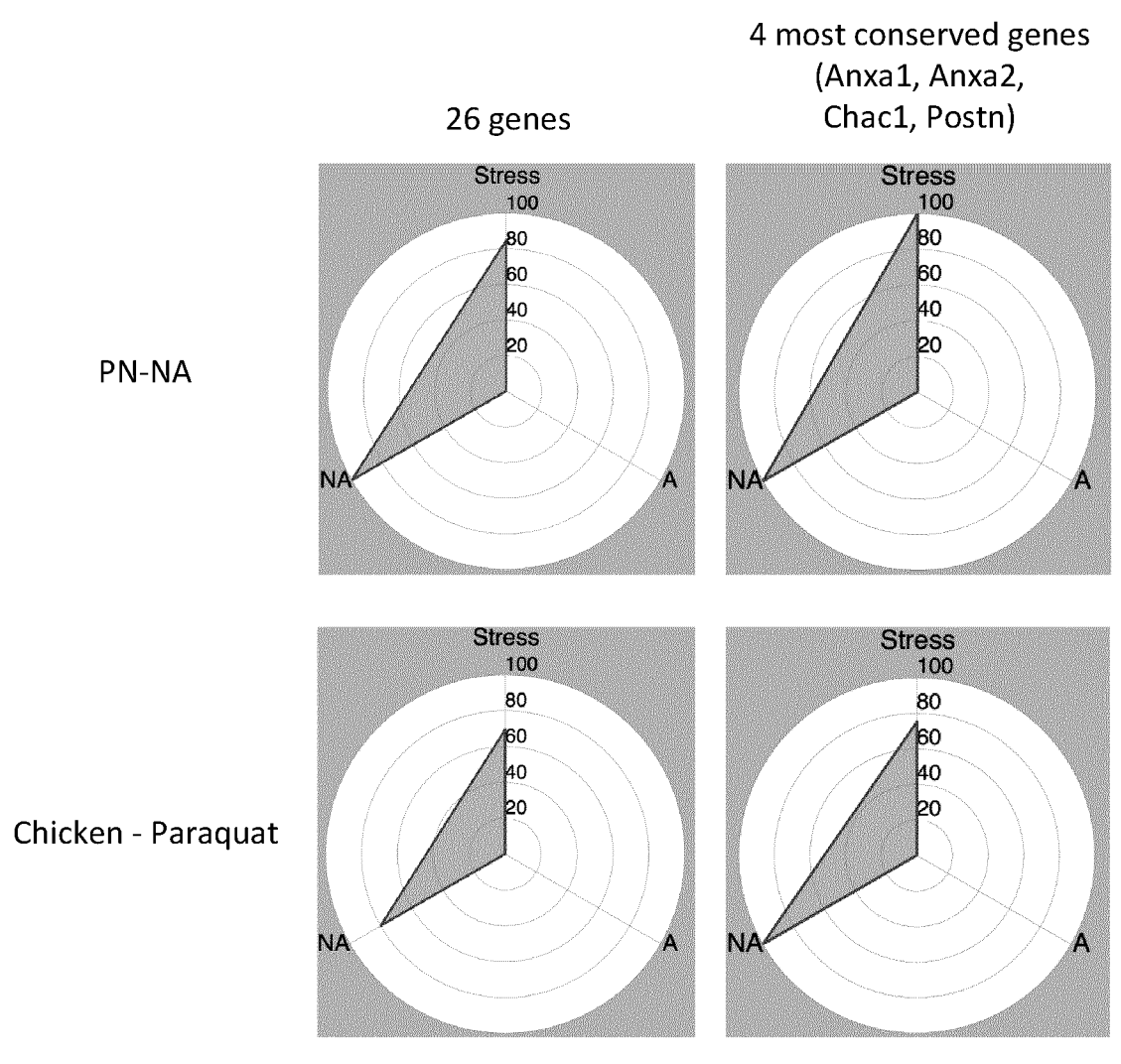
FIG. 5: Radar plot representation of stress score (vertical axis), adaptation score (right axis) and non-adaptation score (left axis), obtained from the computing of a set of differentially expressed genes (left: twenty-six genes; right: four most conserved genes) in stressed animal groups (top: animals of the PN model under non-adaptation (NA) conditions; bottom: chicken exposed to paraquat-induced stress).

The S, NA and A scores, obtained using either the twenty-six genes or the four most conserved genes (Anxa1, Anxa2, Chac1, Postn), in the PN-NA model and in the chicken-paraquat model, are represented in FIG. 5. Similar results were obtained with both signatures. As expected, the PN-NA model was characterized by high stress (S) and non-adaptation (NA) scores, with an adaptation (A) score of 0% (FIG. 5, top). In the chicken-paraquat model, our method evidenced high stress (S) and non-adaptation (NA) scores, using either signature (FIG. 5, bottom). This non-adapted state is in agreement with the weight-loss recorded in the paraquat-treated animals. Overall, these observations, obtained in an animal model different from our four reference animal models, validated the method.

Then, we computed the stress, adaptation and non-adaptation scores obtained with all the 4-gene to 26-gene signatures, which can be derived from the twenty-six genes, in the chicken-paraquat model. Results are presented in Table 4.

The average stress score value for any size of signature was identical to the stress score value obtained with the 26-gene signature, but the standard deviation decreased as the number of genes in the signature increased. For the non-adaptation scores, the mean value was similar (comprised between 78.2% and 80.0%), and the standard deviation also decreased as the number of genes in the signature increased. Concerning the adaptation score, no adaptation state was detected in this model, again in agreement of the weight-loss observed in all stressed animals.

These results show that different signatures of 4- to 26 genes, derived from the twenty-six genes, can be used for identifying the presence or absence of a stress state in a subject, and/or for assessing the stress response level in a subject.

TABLE 4

Stress, non-adaptation and adaptation score values (mean ± standard deviation), computed for different sizes of signatures (from 4 to 26 genes) in the chicken-paraquat model. For reference, scores obtained using the four most conserved genes are indicated in the first line.

| Number of genes in the signature | Number of corresponding signatures | Stress Score (%) | Non-adaptation Score (%) | Adaptation Score (%) |
|---|---|---|---|---|
| 4 most conserved genes | 1 | 75 | 100 | 0 |
| 4 | 14950 | 69.2 ± 21.6 | 78.2 ± 29.5 | 0.0 ± 0.0 |
| 5 | 65780 | 69.2 ± 18.9 | 79.4 ± 24.8 | 0.0 ± 0.0 |
| 6 | 230230 | 69.2 ± 16.8 | 79.8 ± 21.5 | 0.0 ± 0.0 |
| 7 | 657800 | 69.2 ± 15.2 | 79.9 ± 19.0 | 0.0 ± 0.0 |
| 8 | 1562275 | 69.2 ± 13.8 | 80.0 ± 17.0 | 0.0 ± 0.0 |
| 9 | 3124550 | 69.2 ± 12.7 | 80.0 ± 15.4 | 0.0 ± 0.0 |
| 10 | 5311735 | 69.2 ± 11.7 | 80.0 ± 14.1 | 0.0 ± 0.0 |
| 11 | 7726160 | 69.2 ± 10.8 | 80.0 ± 13.0 | 0.0 ± 0.0 |
| 12 | 9657700 | 69.2 ± 10.0 | 80.0 ± 12.0 | 0.0 ± 0.0 |
| 13 | 10400600 | 69.2 ± 9.2 | 80.0 ± 11.0 | 0.0 ± 0.0 |
| 14 | 9657700 | 69.2 ± 8.5 | 80.0 ± 10.2 | 0.0 ± 0.0 |
| 15 | 7726160 | 69.2 ± 7.9 | 80.0 ± 9.4 | 0.0 ± 0.0 |
| 16 | 5311735 | 69.2 ± 7.3 | 80.0 ± 8.7 | 0.0 ± 0.0 |
| 17 | 3124550 | 69.2 ± 6.7 | 80.0 ± 7.9 | 0.0 ± 0.0 |
| 18 | 1562275 | 69.2 ± 6.2 | 80.0 ± 7.3 | 0.0 ± 0.0 |

TABLE 4-continued

Stress, non-adaptation and adaptation score values (mean ± standard deviation), computed for different sizes of signatures (from 4 to 26 genes) in the chicken-paraquat model. For reference, scores obtained using the four most conserved genes are indicated in the first line.

| Number of genes in the signature | Number of corresponding signatures | Stress Score (%) | Non-adaptation Score (%) | Adaptation Score (%) |
|---|---|---|---|---|
| 19 | 657800 | 69.2 ± 5.6 | 80.0 ± 6.6 | 0.0 ± 0.0 |
| 20 | 230230 | 69.2 ± 5.0 | 80.0 ± 6.0 | 0.0 ± 0.0 |
| 21 | 65780 | 69.2 ± 4.5 | 80.0 ± 5.3 | 0.0 ± 0.0 |
| 22 | 14950 | 69.2 ± 3.9 | 80.0 ± 4.6 | 0.0 ± 0.0 |
| 23 | 2600 | 69.2 ± 3.3 | 80.0 ± 3.9 | 0.0 ± 0.0 |
| 24 | 325 | 69.2 ± 2.7 | 80.0 ± 3.1 | 0.0 ± 0.0 |
| 25 | 26 | 69.2 ± 1.8 | 80.0 ± 2.2 | 0.0 ± 0.0 |
| 26 genes | 1 | 69.2 ± 0.0 | 80.0 ± 0.0 | 0.0 ± 0.0 |

The invention claimed is:

1. An in vitro process for identifying the presence or absence of a stress state in a subject being submitted to a challenge and/or for assessing the stress response level in a subject being submitted to a challenge comprising (a) detecting the expression and/or quantifying the expression level, in a sample of said subject, of at least four genes selected from the group consisting of Anxa1, Anxa2, Chac1, and Postn; and (b) administering to the subject at least one intervention solution to reduce or eliminate the stress state and/or stress response level in the subject, wherein the subject and the challenge are selected from:

chickens subjected to heat stress, pigs subjected to heat and inflammatory stress, chickens subjected to a nutritional challenge, and mice subjected to a physical exercise challenge.

2. The in vitro process according to claim 1, wherein said sample is selected from the group consisting of muscle tissue, breast tissue, liver tissue, adipose tissue, skin, lymphoid tissue, placental tissue, gastrointestinal tract tissue, genital tract tissue, central nervous system tissue, spinal cord, ganglion of the trigeminal nerve, urine, feces, feathers, tears, sperm, seminal fluid, cerebrospinal fluid, expectorations, bronchoalveolar lavage fluid, gastric secretions, saliva, serum, plasma and blood.

3. The in vitro process according to claim 1, wherein gene expression is detected and/or quantified at the mRNA level.

4. The in vitro process according to claim 1, wherein gene expression is detected and/or quantified at the protein level.

5. The in vitro process according to claim 4, wherein gene expression is detected and/or quantified by ELISA, Western blot, immunohistochemistry, flow cytometry or proteomics.

6. The in vitro process according to claim 1, further comprising comparing gene expression levels in said sample of said subject with a reference value or with gene expression levels in a reference sample.

* * * * *